United States Patent
Binggeli et al.

(10) Patent No.: US 11,497,233 B2
(45) Date of Patent: Nov. 15, 2022

(54) ENZYMATIC PROCESS

(71) Applicant: GIVAUDAN SA, Vernier (CH)

(72) Inventors: Eva Christina Maria Binggeli, Männedorf (CH); Thomas Kirsch, Cincinnati, OH (US); Surendra Ramchandra Otiv, Plainsboro, NJ (US)

(73) Assignee: GIVAUDAN SA, Vernier (CH)

( * ) Notice: Subject to any disclaimer, the term of this patent is extended or adjusted under 35 U.S.C. 154(b) by 543 days.

(21) Appl. No.: 15/202,047

(22) Filed: Jul. 5, 2016

(65) Prior Publication Data

US 2016/0331010 A1 Nov. 17, 2016

Related U.S. Application Data

(62) Division of application No. 13/972,326, filed on Aug. 21, 2013, now Pat. No. 9,408,408, which is a division of application No. 13/132,981, filed as application No. PCT/CH2009/000392 on Dec. 11, 2009, now Pat. No. 8,580,322.

(60) Provisional application No. 61/122,051, filed on Dec. 12, 2008.

(51) Int. Cl.
*A23L 27/10* (2016.01)
*C12P 7/24* (2006.01)
*A23L 27/12* (2016.01)

(52) U.S. Cl.
CPC .............. *A23L 27/11* (2016.08); *A23L 27/12* (2016.08); *C12P 7/24* (2013.01); *A23V 2002/00* (2013.01)

(58) Field of Classification Search
CPC ......... A23L 27/11; C12P 7/24; A23V 2002/00
USPC ........................................... 426/10
See application file for complete search history.

(56) References Cited

U.S. PATENT DOCUMENTS

| | | | | |
|---|---|---|---|---|
| 2,835,591 A | * | 5/1958 | Graves | A23L 27/11 426/44 |
| 5,202,146 A | * | 4/1993 | Singer | A23L 27/70 426/804 |
| 5,705,205 A | * | 1/1998 | Brunerie | C12P 7/42 426/425 |
| 2005/0074519 A1 | * | 4/2005 | Bartnick | A23L 27/11 426/49 |
| 2005/0074520 A1 | * | 4/2005 | Bartnick | A23L 27/11 426/49 |
| 2007/0281069 A1 | * | 12/2007 | Silverglate | A23C 9/156 426/594 |
| 2008/0181989 A1 | * | 7/2008 | Thomas | A23L 2/02 426/507 |

FOREIGN PATENT DOCUMENTS

| | | |
|---|---|---|
| JP | 10316992 A | 12/1998 |
| WO | 2004091316 A1 | 10/2004 |

OTHER PUBLICATIONS

Technical Bulletin 110. 2007. Biocatalysts; Inc.
Roa, S. R. et al., "Vanilla flavour: production by conventional and biotechnological routes", J. Sci. Fd. Agric. 80: 289-304, 2000.
Randive, "Vanillin and Related Flavor Compounds in Vanilla Extracts Made from Beans of Various Global Origins", J. Agric. Food Chem, 1992, vol. 40, pp. 1922-1924.

* cited by examiner

*Primary Examiner* — Hamid R Badr
(74) *Attorney, Agent, or Firm* — Curatolo Sidoti & Trillis Co., LPA; Salvatore A. Sidoti; Floyd Trillis, III

(57) ABSTRACT

Provided is a process of forming a vanilla extract wherein green ripe vanilla beans are exposed to a high drying temperature, extracted with a solvent, and treated with beta-glucosidase enzyme to convert glucovanillin to vanillin enzymatically, thereby providing a vanilla extract with a good vanillin yield and complex well-balanced vanilla aroma lacking undesirable off-notes.

3 Claims, No Drawings

ENZYMATIC PROCESS

This is a divisional patent application of U.S. Ser. No. 13/972,326 filed 21 Aug. 2013, which in turn is a divisional patent application of copending U.S. Ser. No. 13/132,981, which in turn is an application filed under 35 USC 371 of PCT/CH2009/000392, claiming priority to U.S. Ser. No. 61/122,051 filed 12 Dec. 2008; the entirety of the foregoing documents are herein fully incorporated by reference thereto, and the applicant claims the full priority benefit of their priority application.

TECHNICAL FIELD

Disclosed is an enzymatic process of forming a vanilla extract from green ripe vanilla beans which are dried during exposure to heat and then exposed to a beta-glucosidase enzyme to convert glucovanillin to vanillin.

BACKGROUND

Vanilla extracts comprising vanillin and other flavor compounds are produced by subjecting ripe green vanilla beans to a curing and extraction process. The curing process forms the brown-black whole vanilla beans available in the super markets. The cured beans can than be extracted to form a liquid vanilla extract.

The enzymatic reactions in the vanilla beans from its precursor glucovanillin to vanillin are believed to be mainly caused by residual plant enzymes, in particular glucosidase enzymes.

The glucovanillin content in perfectly matured vanilla beans is about 10% per weight of dried vanilla beans on average, which can be theoretically converted into a maximum of 4.84% vanillin assuming complete conversion and no losses. Usually, much lower yields are obtained, especially in traditional processes.

Traditional so-called "curing" processes involve scalding, sweating and a long conditioning step that lasts several weeks or months and employs naturally occurring enzymatic reactions.

Prior to sweating and conditioning, the beans usually are subjected to a short (e.g. three minutes) step of scalding in hot water at about 65° C.

During the sweating step, exposure to heat in a humid atmosphere to prevent drying out of beans allows naturally occurring enzymes to convert various precursors including glucovanillin to vanilla flavor components including vanillin.

During the conditioning period which usually lasts many weeks or months, the beans are very slowly dried to allow natural enzymatic reactions to continue. This step involves repeated quality controls and depends on the environmental conditions.

While the sensory profile/flavor of the resulting extracts can be excellent, even under optimal conditions the vanillin yield is very low and usually up to about 2.2% per dry weight of vanilla beans.

Less time consuming processes known in the art either result in a similarly low average vanillin yield, and/or the sensory profile is not acceptable, lacking in complex vanilla aroma and/or containing undesirable off-notes to an extent that almost completely overpowers the vanillin taste even if the yield of vanillin is relatively high, and results in an artificial note not associated with the typical aroma of a vanilla extract formed by traditional several months long curing methods.

For example, some known shorter processes add enzymes to green vanilla beans, for example as described in WO 2004/091316 and U.S. Pat. No. 5,705,205.

WO 2004/091316 describes a combined treatment of extraction and subsequent enzymatic reaction based on green vanilla beans. The enzymatic process employs enzymes with a high lytic activity and a marked cellulase activity (unlike for example beta-glucosidase). These lytic enzymes are used to release the vanillin formed during browning from the plant cells by lysis of the plant cell walls. The accelerated browning step of 0.5 to 7 days is performed by freezing of green vanilla beans followed by thawing, or alternatively, when accepting a lower vanillin yield, by shortly scalding in water at 60° C. to 65° C. and a subsequent sweating step, incubating the scalded beans at 15° C. to 45° C. until brown for a similar time.

U.S. Pat. No. 5,705,205 describes an enzymatic process wherein green freshly harvested beans are hydrated to be ground in water and subjected to various enzymes including, among others, β-glucosidase, the latter to hydrolyze glucovanillin to vanillin.

While improved organoleptically when compared to some earlier enzymatic processes, ripe green (i.e. "uncured") vanilla beans processed according to known enzymatic processes of short duration (several days up to about a week) still do not develop a comparably complex aroma when compared to traditional curing processes that last for several weeks or months.

Accordingly, there remains a need for a short process that can provide a vanilla bean extract with a good vanillin yield, with an improved sensory profile having a more complex vanilla aroma without off-notes.

In particular, a complex vanilla aroma should comprise a low concentration of desirable phenolic notes (as they will be perceived to be overpowering otherwise), and lack or minimize the very dominant fatty acid off-notes and green off-notes often associated with extracts made from green vanilla beans (rather than cured vanilla beans).

Both traditional curing and the shorter enzymatic processes keep the vanilla beans moist for a significant duration of the process to allow the residual plant enzymes and/or added enzymes to do their work, converting glucovanillin to vanillin.

SUMMARY

Applicant discovered that when green vanilla beans are first dried quickly within about 24 hours to a low moisture content of about 10%, and only afterwards subjected to an enzymatic treatment employing b-glucosidase, vanilla extracts with a good vanillin yield and a complex well-balanced vanilla aroma without off-notes can be formed.

Provided is the following:
(1) A process of forming a vanilla extract comprising
a) forming dried vanilla beans by comminuting green ripe vanilla beans and incubating them at a drying temperature of about 65° C. to about 120° C. for about 5 to about 24 hours in an environment where moisture can escape until a moisture content of less than 10% is reached,
b) grinding or finely chopping the dried vanilla beans,
c) incubating the dried vanilla beans, or an extract thereof, with one or more beta-glucosidase enzyme provided as an additive, to convert glucovanillin to vanillin, and
d) extracting the dried ground vanilla beans with a solvent before or after step c).

(2) The process as described herein, including under (1), wherein the extraction step b) is performed prior to the enzyme incubation step c).
(3) The process as described herein, including under any one of (1) and (2), wherein the resulting vanilla extract of step b) is concentrated by at least partly removing the solvent.
(4) The process as described herein, including under any one of (1) to (3), wherein the mixture of step c) is concentrated at a maximum temperature of about 45° C.
(5) The process as described herein, including under any one of (1) to (4), wherein the volume of the extract is adjusted by adding a food-grade solvent to achieve the desired concentration of vanilla extract.
(6) The process as described herein, including under any one of (1) to (5), wherein the drying temperature is about 80 to about 90° C.
(7) The process as described herein, including under any one of (1) to (6), wherein the solvent is selected from the group consisting of water, ethanol, hexane, or mixtures thereof.
(8) The process as described herein, including under any one of (1) to (7), wherein the glucovanillin concentration of the green ripe vanilla beans is at least 6% (wt/wt).
(9) The process as described herein, including under any one of (1) to (8), wherein the amount of the enzyme in step d) is equal to 0.005 to 0.2 times the vanilla bean charge weight.
(10) The process as described herein, including under any one of (1) to (9), wherein the temperature in step c) is about 20° C. to about 80° C.
(11) The process as described herein, including under any one of (1) to (10), wherein the incubation time in step c) is 10 hour to 2 days.
(12) The process as described herein, including under (11), wherein the incubation time in step c) 16 to 24 hours.

DETAILED DESCRIPTION

In a first step, dried vanilla beans are formed by comminuting green ripe vanilla beans and drying them at a drying temperature of about 65° C. to about 120° C. for about 5 to about 24 hours in an environment where moisture can escape until a moisture content of less than 10% (w/w) is reached.

Applicant has discovered that when green uncured beans are first dried quickly and only afterwards treated enzymatically in an enzymatic process of about 10 to 48 h, for example 16 to 24 hours, a vanilla extract having a complex well-balanced vanilla aroma similar to that formed by traditionally curing beans, which includes a low concentration of phenolic notes, and is lacking in off-notes, in particular fatty acid and green off-notes, can be provided.

An extract can be formed prior to the enzymatic reaction, which has the additional benefit of eliminating plant-derived fibers, which may cause problems including lowering the total yield of vanilla extract, including vanillin yield, and furthermore may require additional downstream processing steps (for example, additional filtration). Alternatively, the enzymatically processed vanilla bean material can be extracted afterwards.

Furthermore, without wishing to be bound by theory, applicant discovered that one factor on vanillin yield of vanilla beans is the presence of certain bacteria. The first heating/drying step also contributes to reduce these microorganisms and avoids the early formation of vanillin (which appears to be formed to a significant extent by bacterial enzymes rather than plant enzymes), thereby avoiding the degradation of vanillin by microorganisms that sets in at higher vanillin concentrations, to avoid its toxicity. Therefore, to maximize yield, the beans should be dried to a moisture content of about 10% as quickly as possible.

Optionally, to further maximize vanillin yield, the process may be performed with vanilla beans high in glucovanillin (i.e. high in vanillin precursor but low in vanillin). Ideally, the glucovanillin should be at least 6% or higher, for example at least 7%, at least 8%, or at least 10%. Accordingly, beans from *Vanilla planifolia* are preferred, while beans from *V. pompona*, and *V. tahitensis* usually do not have a sufficient glucovanillin concentration.

Optionally, to ensure the development of a fully-developed well-balanced complex aroma the extraction steps should be performed before conversion of glucovanillin to vanillin (rather than afterwards). Again without wishing to be bound by theory, the extraction prior to the enzymatic incubation reduces the microorganisms otherwise present during the enzyme treatment which appears to contribute to the development of a well-balanced complex aroma.

The vanilla bean products including, without limitation, vanilla extracts described herein provide a well-developed, well-balanced complex flavor profile comprising the major vanilla flavor compounds. Major vanilla flavor compounds include, without limitation, phenolic compounds, furan compounds, fatty acid compounds, compounds formed by reaction with ethanol, and acetaldehyde diethyl acetal.

Phenolic vanilla flavor compounds include, without limitation, acetovanillone alpha-ethoxy-p-cresol, benzoic acid, guaiacol, 4-methylguaiacol, p-hydroxybenzaldehyde, methylparaben, methyl vanillate, 2-methoxy-4-vinylphenol 5-methoxyvanillin, phenol, Vanillin, vanillic acid, vanillyl alcohol, vanillyl ethyl ether, and p-vinylphenol.

These phenolic vanilla flavor compounds, in particular guaiacol, should be present in a low concentration so that they do not dominate resulting in an unbalanced flavor.

Furan vanilla flavor compounds include, without limitation, 2-furfural, 2-furfurol 5-(hydroxymethyl)-2-furfural, 5-methyl-2-furfural, 2-hydroxyfuraneol, gamma-butyrolactone (dihydro 2(3H)-furanone).

Fatty acid vanilla flavor compounds include, without limitation, linoleic acid, and palmitic acid.

Vanilla flavor compounds that are formed by the reaction with ethanol include, without limitation, etyl acetate, ethyl glycolyte, ethyl lactate, ethyl linoleate, ethyl pyrovate, ethyl levulinate, and diethylsuccinate.

A vanilla extract consists substantially of extractive matter of vanilla beans from plants of the genus vanilla, and optionally a solvent. For example, certain sugars may be added in some countries. Solvents include, without limitation, alcohol/ethanol, and water. Solvents that are not food grade have to be removed or sufficiently reduced in concentration to form the end product sold to the consumer according to nationally differing regulatory requirements.

There are currently three major cultivars of the genus vanilla grown globally, all derived from a species originally found in Mesoamerica: *Vanilla planifolia* (*V. planifolia*, syn. *V. fragrans*), grown on Madagascar, Réunion and other tropical areas along the Indian Ocean; *V. tahitensis*, grown in the South Pacific; and *V. pompona*, found in the West Indies, Central and South America. The majority of the world's vanilla that is produced is the *V. planifolia* variety, grown in a small region of the east African nation of Madagascar and Indonesia, and which when produced in Madagascar is more commonly known as "Madagascar-Bourbon" vanilla.

Vanilla spec. include, without limitation, *V. planifolia, V. tahitensis, V. pompona*, and hybrids of these or other vanilla spec. plants, for example, without limitation, hybrids of *V. planifolia* and *V. pompona*.

Vanilla beans require about 6 months to fully develop on the vine, during which stage the beans are green in color. At the end of the growing stage the beans are still green with a small yellow tip and sometimes referred to as "blossom-end yellow" or "mature", which is the stage at which mature or ripe green beans are harvested. When traditionally cured, they turn from green to brown. A green vanilla bean therefore is a mature uncured bean. The green ripe vanilla beans should be completely ripe for maximum glucovanillin content. This can be tested by visual inspection (green beans with yellow tip). To further optimize yield, the glucovanillin concentration may be tested. A suitable glucovanillin concentration is from about 6% or higher.

The vanilla beans are comminuted by any suitable means to render them to pieces, for example, without limitation, about 1-2.5 cm long. Any suitable tool or mechanism may be employed. For example, the beans may be cut or chopped. The cuts generally proceed transversely of the long axes of the beans though other directions are possible as well.

The process of forming a vanilla extract comprises drying comminuted green ripe beans at a drying temperature of about 65° C. to about 120° C. for at least about one hour or until a moisture content of less than 10% is reached. A suitable drying temperature, for example, includes from about 80° C. to 90° C. Drying may be facilitated by forced air, applying a vacuum, or any other means that do not burn or roast the beans. The temperature needs to be high enough to reduce vanillin-degrading microorganisms, including, without limitation, *Bacillus subtilis*, for example, 65° C. and above, but below a temperature where the beans burn. The latter will also depend on the residual moisture content that will drop during the drying process, e.g. drying can be started at 120° C. but the temperature will be adjusted to a lower temperature of 65° C. to 100° C. once the beans are drier and before they start to burn. The beans should reach a moisture concentration of less than 10% (w/w). Moisture content can be easily determined, e.g. using an infrared oven/moisture analyzer and weighing before and after drying, comparing a partially dried bean to a ground and completely dried bean. Depending on the initial temperature and degree of temperature reduction during drying, the duration of drying will vary. It usually takes not more than 24 hours, which is sufficient time to reduce the microorganisms to an acceptable level so that produced vanillin is not significantly degraded in the subsequent steps including during the enzymatic reaction. If more time is available, whole beans may be dried more slowly at a lower temperature, for example at about 60° C., but this is less preferred since it will allow more microbial organisms, including *Bacillus subtilis*, to survive and thereby lower vanillin yield.

The dried vanilla beans are ground in a grinder and extracted with a solvent.

Any solvent able to bring vanillin and/or additional vanilla flavors into solution can be used. Useful solvents include water and alcohols, including without limitation organic alcohols. Organic alcohols include, without limitation, alkanols having up to 4 carbon atoms, for example, ethanol, isopropanol, propanol, low molecular weight glycols and polyols including, without limitation, propylene glycol, butylene glycol, or glycerin, or mixtures thereof.

Suitable solvents include, without limitation, aqueous alcohol solvents containing at least one alcohol miscible with water in the proportions employed. Suitable aqueous alcohol solvent includes, without limitation, mixtures of ethanol and water, for example, ethanol/water (50:50).

If a food-grade solvent is used it does not need to be removed afterwards, which is more efficient particularly in the final process steps. Food-grade solvents include, without limitation, ethanol, water, mixtures of ethanol and water, ethanol/water (50:50), and mixtures thereof. Another alternative may be supercritical fluid extraction.

Solvents that are not food-grade, or not food-grade in all legislations or in all concentrations for all end products, for example, without limitation, hexane, ethylmethylketone, methyl acetate, dichloromethane, fusel oil, or mixtures thereof, have to be either completely removed or at least partially removed (to a specific low concentration that usually varies according to the national food regulations) to form the end product sold to the consumer. The term "fusel oil" designates a distilled concentrated liquid obtained in small amounts as a by-product of alcoholic fermentation and distillation that consists of a mixture chiefly of alcohols, such as isopentyl alcohol, amyl alcohol, isobutyl alcohol, isopropyl alcohol and propyl alcohol.

Optionally, the resulting vanilla extract can be concentrated by at least partly removing the solvent.

When part of the solvent is not water, for example, without limitation, ethanol, the non-water part of the solvent needs to be at least partially removed prior to incubation with beta-glucosidase enzyme, for example, to an ethanol concentration of less than 25%. Low molecular weight glycols and polyols usually influence enzymatic activity less and may remain in concentrations that do not negatively influence the beta-glucosidase enzyme.

After the enzymatic conversion to vanillin, the extract may optionally be concentrated, for example, without limitation, by heating in a destillator under vacuum. The extract should not be heated too high to avoid degradation of vanillin. Temperatures of up to 45° C. during concentration of the extract usually do not negatively influence the vanillin yield significantly.

Optionally, the volume of the vanilla extract may be adjusted as desired by adding a solvent as described herein to achieve the desired fold vanilla extract.

The vanilla extract is subjected to an enzymatic reaction using a beta-glucosidase enzyme (commercially available from various sources including Biocatalysts Limited, Cardiff, UK) or a mixture containing a beta-glucosidase enzyme and optionally additional enzymes. The amount of beta-glucosidase enzyme depends on the incubation parameters including duration, temperature, amount and concentration of substrate and of solvent.

Too much enzyme will not have an additional benefit and may introduce off-tastes. To little enzyme will lengthen the time required for the enzymatic process to reach an acceptable vanillin yield. The optimal amount of enzyme can be easily determined and adjusted accordingly.

If a mixture of enzymes containing 5 units per g of beta-glucosidase is used, then an amount of enzyme 0.005 to 0.2 times the vanilla bean charge weight is usually sufficient, for example, without limitation, 0.02 to 0.1, or 0.035 to 0.15 times.

A suitable solvent to use in the enzyme incubation includes water and mixtures of water with another solvent compatible with the enzyme. For example, ethanol should be less than 25% for optimal enzymatic reaction.

The enzyme is incubated within a suitable temperature range, for example, 20° C. to 80° C. or 40° C. to 60° C., for example, without limitation, near its temperature optimum at about 55° C. to 60° C., and held at this temperature for a sufficient time to convert glucovanillin to the desired vanillin yield. Continuous stirring will ensure a constant temperature and concentrations. Smaller volumes may not require stirring.

The incubation time will depend on the amount and concentration of the enzyme and substrate, solvent present, temperature chosen, for example, without limitation, 1 hour to 2 days or longer. Usually, 24 hours are sufficient.

Preferably, the mixture should be stirred during the enzymatic reaction to ensure sufficient mixing, constant temperature throughout the reaction vessel, and access of enzyme to substrate.

After the enzymatic incubation, optionally, the vanilla extract may be concentrated as is well known in the art, for example in a destillator under vacuum. The temperature should not exceed a maximum of about 45° C. to avoid any partial degradation of vanillin.

Optionally, food-grade solvent may be added to adjust the concentration or so-called fold of the vanilla extract end product as desired.

EXAMPLES

Unless otherwise indicated, percentages are given as wt/wt and all ingredients and solvents are food grade. Vanilla beans were from *Vanilla planifolia* plants. Vanilla extracts below use the US "fold" unit, e.g. a single-fold vanilla extract is one which contains the extractive matter of one unit of vanilla beans (13.35 oz vanilla pods with a maximum moisture content of 25%) in one US gallon (35% alcohol) of product. Thus, a ten-fold vanilla extract is one which contains the extractive matter of ten units of vanilla beans per US gallon of finished product according to the FDA, Title 21.

Example 1

Preparation of a High Vanillin Vanilla Extract

Preparation of dried green vanilla beans:

Green fully ripe vanilla beans with a high concentration (at least 6%-10% or higher based on the dried weight of beans; usually green beans have about 16% dry substance, and after drying, about 90% dry substance) of glucovanillin determined by visual inspection (green bean with yellow tip) were used. Drying was performed by cutting the beans into pieces of about 2.5 cm length, and then drying at about 85° C. (80° C. to 90° C.) in an oven until a moisture concentration of less than 10% was reached. The moisture percentage was determined using an infrared oven (Moisture Analyzer, Computrac, Model Max-1000, by Arizona Instruments) and weighing the beans before and after drying. The drying procedure usually took about 10 to 20 hours. This reduced the microorganims to an acceptable level so that produced vanillin was not significantly degraded during the enzymatic reaction.

Dried beans were ground in a grinder (Mr Coffee, Cleveland Ohio, USA).

1.59 kg (or 3.5 lbs) of ground vanilla beans were extracted and concentrated to give 1 times the vanilla bean charge weight of the resulting extract. Vanilla beans were extracted five times with 50/50 (w/w) tap water and ethanol 2.27 kg or 5 lbs of solvent per extraction. The combined extracts were concentrated under vacuum with a maximum temperature of 45° C. to 1.35 times the vanilla bean charge weight to remove the ethanol solvent. Tap water was added to bring the total weight to 6.86 times the vanilla bean charge weight.

Depol 40 L enzyme mix, containing a high concentration of beta-glucosidase (Biocatalysts Limited, Cardiff, UK), was added in an amount equal to 0.0686 times the vanilla bean charge weight. The mixture with enzyme was heated to 60° C. and held at this temperature for 16 hours while continuously stirring. After the enzymatic reaction, the mixture was cooled to 45° C. or lower, and concentrated in a destillator to 0.71 times the bean charge weight under vacuum at a maximum temperature of 45° C. to avoid degradation of vanillin.

Ethanol was added to adjust to about 40% (v/v) ethanol (about 0.3 times the vanilla bean charge weight) to achieve a final weight of the resulting clear 10 fold vanilla extract equal to 1 times the vanilla bean charge weight.

The glucovanillin concentration of the green vanilla beans on a dried-weight basis before enzyme treatment was measured at 5.9% (w/w), and the vanillin concentration at 0.9%. Accordingly, the calculated maximal vanillin yield was 3.76 (w/w, dried-weight basis) (glucovanillin concentration multiplied with 0.484 plus initial vanillin concentration) assuming an only theoretically obtainable 100% vanillin yield based on complete conversion of glucovanillin without any degradation (known vanillin yielding processes usually reach not more than about 90% of the theoretically obtainable maximum vanillin yield due to losses during recovery of formed vanillin).

In the 10 fold vanilla extract, the vanillin yield obtained was measured by high performance liquid chromatography (HPLC) at 3.0% (w/w) and the glucovanillin concentration was measured at 0.36% (w/w) based on the weight of the processed dried vanilla beans.

Accordingly, the achieved vanillin yield (3%) corresponded to 80% of the theoretically possible maximal vanillin yield (3.7%).

Example 2

Modified Process—Enzyme Treatment Prior to Extraction

The dried ground beans were prepared as described in example 1 above.

22 lbs (9.979 kg) of the dried and ground beans were added to 110 lbs (49.895 kg) of water in a stirred tank, and heated to 85° C. for 1 hour. The resulting mixture was cooled to 60° C. 1.1 lbs (0.499 kg) of Depot 40 L was added. The resulting mixture was stirred for 18 hours at 60° C., then cooled to 50° C. The pH was adjusted to pH 7 by the addition of 50% sodium hydroxide 110 lbs (49.895 kg) of ethanol was added to this mixture and mixed for 4 hours at 50° C. then cooled to 25° C. The extract was decanted and set aside. Four more extractions were performed at 50° C. with a mixture of 44 lbs (19.958 kg) ethanol and 44 lbs (19.958 kg) water. After each extraction the extract was decanted and set aside. The combined extracts were concentrated under vacuum with a maximum temperature of 45° C. to 1.35 times the vanilla bean charge weight to remove the ethanol solvent.

Ethanol was added to adjust to about 40% (v/v) ethanol (about 0.3 times the vanilla bean charge weight) to achieve a final weight of the resulting clear 10 fold vanilla extract equal to 1 times the vanilla bean charge weight.

The glucovanillin concentration of the green vanilla beans on a dried-weight basis before enzyme treatment was measured at 7.1% (w/w), and the vanillin concentration was 0.4% (w/w).

Accordingly, the calculated maximal vanillin yield was 3.85% (w/w, dried-weight basis, 3.44% from glucovanillin precursor and 0.4 already existing vanillin) assuming an only theoretically obtainable 100% vanillin yield based on complete conversion of glucovanillin without any degradation.

In the 10 fold vanilla extract, the vanillin yield obtained was measured at 3.28% (w/w) and the glucovanillin concentration was measured at 0.10% (w/w) based on the weight of the processed dried vanilla beans.

Accordingly, the achieved vanillin yield (3.28%) corresponded to 85% of the theoretically obtainable maximum vanillin yield (3.84%).

Comparative Example 3

Modified Process as in Example 2 but without Drying of the Green Vanilla Beans

The process of example 2 was essentially repeated except for the heating and drying steps of the green vanilla beans, which were left out.

2 kg green vanilla beans (not subjected to a drying process) with a dry substance of 16% in 10 liters of water were chopped, treated enzymatically, and extracted as described in example 2. The amount of water that was added upon extraction was adjusted accordingly.

The glucovanillin concentration of the green vanilla beans on a dried-weight basis before enzyme treatment was measured at 6.9% (w/w), and the vanillin concentration was 1.9% (w/w).

Accordingly, the calculated maximal vanillin yield was 5.2% (w/w, dried-weight basis).

In the 10 fold vanilla extract, the vanillin yield was measured by HPLC at 3.2% (w/w) and the glucovanillin concentration was measured at 0% (w/w) (indicating a complete degradation and conversion of glucovanillin) based on the weight of the processed dried vanilla beans.

Accordingly, the achieved vanillin yield (3.2%) corresponded to 61% of the theoretically obtainable maximum vanillin yield (6.9%).

Example 4

Sensory Evaluation 0.15 ml of the 10 fold vanilla extracts of example 1, 2 or 3 and as a control a commercially available 10 fold extract from traditionally cured vanilla beans (subjected to a standard curing process over several months) were added to 100 ml of sweetened milk (5% sucrose) and compared in a sensory evaluation by trained panelists.

Panelists described the aroma of the example 1 vanilla extract and the control as having a balanced, well-rounded, complex, clean-tasting vanilla aroma with a strong vanillin impact without off-tastes such as fatty acid off-tastes nor green off-tastes, and low in phenolic notes (the latter are undesirable in higher concentrations).

Comparing the example 1 extract and the control, the example 1 extract had more vanillin impact and less phenolic notes but a vanilla aroma otherwise comparable to the control, which in contrast had stronger undesirable phenolic notes.

The example 2 vanilla extract was very similar organoleptically to example 1 but slightly less preferred.

The example 3 vanilla extract (without drying step) was clearly the least preferred extract, and was very different in aroma both from the control and from example 1 and 2. It was described as having a vanillin note missing the complexity of additional vanilla aroma compounds, with strong off-tastes of fatty acids such as oleic acid and linolic acid as well as green note off-tastes contributing to an undesirable artificial note that almost completely overpowers the vanillin note.

While the processes have been described above in connection with certain illustrative embodiments, it is to be understood that other similar embodiments may be used or modifications and additions may be made to the described embodiments for performing the same function(s). Further, all embodiments disclosed are not necessarily in the alternative, as various embodiments may be combined to provide the desired characteristics. Variations can be made by one having ordinary skill in the art without departing from the spirit and scope of the disclosure. Therefore, the processes should not be limited to any single embodiment, but rather construed in breadth and scope in accordance with the recitation of the attached claims.

The invention claimed is:

1. A method for making a beverage comprising a vanilla extract, wherein the vanilla extract is produced by steps a)-c):
   a) preparing dried vanilla beans by comminuting green ripe vanilla beans and incubating them at a drying temperature of about 65° C. to about 120° C. for about 5 to about 24 hours in an environment where moisture can escape until a moisture content of less than 10% is reached,
   b) incubating the dried vanilla beans, or an extract thereof, with one or more beta-glucosidase enzyme provided as an additive, to convert glucovanillin to vanillin, and
   c) extracting the dried vanilla beans or the incubated vanilla beans with a solvent before or after step b);
   and adding the vanilla extract to the beverage.

2. The method of claim 1, wherein the process includes the additional process step of: adjusting the volume of the vanilla extract by adding a food-grade solvent thereto to achieve a desired concentration of vanilla extract.

3. The method of claim 1, in which step c) is the step: c) extracting the dried vanilla beans with a solvent prior to the enzyme incubation step b).

* * * * *